(12) United States Patent
Griffith

(10) Patent No.: US 8,897,883 B2
(45) Date of Patent: Nov. 25, 2014

(54) COCHLEAR IMPLANT SYSTEMS INCLUDING MAGNETIC FLUX REDIRECTION MEANS

(75) Inventor: Glen A. Griffith, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 436 days.

(21) Appl. No.: 13/128,755

(22) PCT Filed: Nov. 11, 2009

(86) PCT No.: PCT/US2009/064033
§ 371 (c)(1),
(2), (4) Date: May 11, 2011

(87) PCT Pub. No.: WO2010/056751
PCT Pub. Date: May 20, 2010

(65) Prior Publication Data
US 2011/0224789 A1    Sep. 15, 2011

Related U.S. Application Data

(60) Provisional application No. 61/113,675, filed on Nov. 12, 2008, provisional application No. 61/113,708, filed on Nov. 12, 2008, provisional application No. 61/139,567, filed on Dec. 20, 2008.

(51) Int. Cl.
| | | |
|---|---|---|
| *A61F 11/04* | (2006.01) |
| *A61N 1/378* | (2006.01) |
| *A61N 1/372* | (2006.01) |
| *H01Q 7/00* | (2006.01) |
| *A61N 1/36* | (2006.01) |
| *H01Q 17/00* | (2006.01) |
| *H01Q 1/27* | (2006.01) |
| *A61N 1/37* | (2006.01) |
| *A61N 1/375* | (2006.01) |

(52) U.S. Cl.
CPC ........ *A61N 1/36032* (2013.01); *A61N 1/37229* (2013.01); *A61N 1/3718* (2013.01); *A61N 1/3758* (2013.01); *H01Q 7/00* (2013.01); *H01Q 17/001* (2013.01); *H01Q 1/273* (2013.01); *A61N 1/3787* (2013.01)
USPC .............................................. 607/57; 607/61

(58) Field of Classification Search
USPC ........................................ 607/55–57, 61, 116
See application file for complete search history.

(56) References Cited

U.S. PATENT DOCUMENTS

| | | | |
|---|---|---|---|
| 4,819,647 A | | 4/1989 | Byers et al. |
| 5,571,148 A | * | 11/1996 | Loeb et al. ...................... 607/57 |

(Continued)

OTHER PUBLICATIONS

Extended European Search Report received in European Patent Application No. 09826674.5, dated Aug. 16, 2012.

(Continued)

*Primary Examiner* — Carl H Layno
*Assistant Examiner* — Jon Eric C Morales
(74) *Attorney, Agent, or Firm* — ALG Intellectual Property, LLC

(57) ABSTRACT

Cochlear implant systems include a circuit board having electronic circuitry configured to generate one or more signals configured to direct electrical stimulation of one or more stimulation sites within a patient, an induction coil configured to transmit a telemetry signal by generating a telemetry magnetic field, and a telemetry flux guide positioned between the induction coil and the circuit board. The telemetry flux guide is configured to direct magnetic flux of the telemetry magnetic field away from the circuit board.

21 Claims, 7 Drawing Sheets

(56) References Cited

U.S. PATENT DOCUMENTS

| | | |
|---|---|---|
| 6,067,474 A | 5/2000 | Schulman et al. |
| 6,218,753 B1 | 4/2001 | Asano et al. |
| 6,219,580 B1 | 4/2001 | Faltys et al. |
| 6,272,382 B1 | 8/2001 | Faltys et al. |
| 6,308,101 B1 | 10/2001 | Faltys et al. |
| 6,389,318 B1 | 5/2002 | Zarinetchi et al. |
| 7,945,334 B2 | 5/2011 | Jimenez et al. |
| 2002/0032472 A1 | 3/2002 | Zarinetchi et al. |
| 2004/0249428 A1* | 12/2004 | Wang et al. .................. 607/116 |
| 2005/0113888 A1* | 5/2005 | Jimenez et al. ................ 607/61 |
| 2006/0190059 A1 | 8/2006 | Griffith |
| 2008/0002834 A1 | 1/2008 | Hochmair |
| 2011/0009924 A1* | 1/2011 | Meskens ........................ 607/57 |

OTHER PUBLICATIONS

International Search Report and Written Opinion received in International Application No. PCT/US09/64033 dated Jan. 12, 2010.

* cited by examiner

COCHLEAR IMPLANT SYSTEMS INCLUDING MAGNETIC FLUX REDIRECTION MEANS

RELATED APPLICATIONS

The present application claims priority to U.S. Provisional Patent Application No. 61/113,675 by Scott A. Crawford et al., filed on Nov. 12, 2008, and entitled "Integrated Cochlear Implant Headpiece," U.S. Provisional Patent Application No. 61/113,708 by Scott A. Crawford et al., filed on Nov. 12, 2008, and entitled "Modular Speech Processor Headpiece," and U.S. Provisional Patent Application No. 61/139,567 by Glen A. Griffith, filed on Dec. 20, 2008, and entitled "Cochlear Implant Systems Including Magnetic Flux Redirection Means." The contents of all of these applications are incorporated herein by reference in their respective entireties.

BACKGROUND

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce audio signals into auditory nerve impulses. Thus, many people who suffer from severe to profound sensorineural hearing loss are unable to derive any benefit from conventional hearing aid systems. To overcome sensorineural hearing loss, numerous cochlear implant systems, or cochlear prosthesis, have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

Cochlear implant systems typically include a cochlear stimulator that is implanted beneath the scalp of a patient. An external control assembly located external to the patient's scalp may be used by the patient to control and adjust various operational parameters of the implanted cochlear stimulator. An inductive link is commonly used to transmit telemetry signals from the external control assembly to the implanted cochlear stimulator. To this end, the external control assembly often includes an inductive coil that produces a telemetry signal by generating an electromagnetic field that is picked up by a receiver on the implanted cochlear stimulator. The inductive coil may be housed in an external headpiece that is positioned on a patient's head to transmit the telemetry signal through the patient's scalp to the implanted receiver. The external control often includes a retention magnet for securing the headpiece to the patient's head so that the induction coil is properly positioned adjacent to the implanted receiver.

In a conventional cochlear implant system, electronic circuitry included within the external control assembly is not placed in relative close proximity to the induction coil and the retention magnet due to losses and interference caused by magnetic flux associated with the induction coil and the retention magnet. Hence, the electronic circuitry is typically housed within a behind-the-ear unit, for example, while the induction coil and the retention magnet are housed separately within a headpiece. Such a configuration is undesirable for many cochlear implant patients.

SUMMARY

Exemplary cochlear implant systems include a circuit board having electronic circuitry configured to generate one or more signals configured to direct electrical stimulation of one or more stimulation sites within a patient, an induction coil configured to transmit a telemetry signal by generating a telemetry magnetic field, and a telemetry flux guide positioned between the induction coil and the circuit board. The telemetry flux guide is configured to direct magnetic flux of the telemetry magnetic field away from the circuit board.

Exemplary cochlear implant systems include a circuit board having electronic circuitry configured to generate one or more signals configured to direct electrical stimulation of one or more stimulation sites within a patient, a retention magnet configured to produce a retention magnetic field for securing one or more components of the cochlear implant system to a head of said patient, and a retention flux guide positioned between the retention magnet and the circuit board. The retention flux guide is configured to direct magnetic flux of the retention magnetic field away from the circuit board.

Exemplary external headpieces for use in cochlear implant systems include a circuit board having electronic circuitry configured to generate one or more signals configured to direct electrical stimulation of one or more stimulation sites within a patient. The external headpieces further include an induction coil configured to transmit a telemetry signal by generating a telemetry magnetic field and a telemetry flux guide positioned between the induction coil and the circuit board. The telemetry flux guide is configured to direct magnetic flux of the telemetry magnetic field away from the circuit board.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Cochlear implant systems including an external headpiece that houses a circuit board having electronic circuitry configured to generate one or more signals configured to control an operation of an implantable cochlear stimulator are described herein. The external headpiece further includes an induction coil configured to transmit a telemetry signal to the implantable cochlear stimulator by generating a telemetry magnetic field. The external headpiece may additionally include a telemetry flux guide positioned between the induction coil and the circuit board. The telemetry flux guide may be configured to direct magnetic flux of the telemetry magnetic field away from the circuit board.

In some examples, the external headpiece further includes a retention magnet configured to produce a retention magnetic field for securing the headpiece to a head of the patient. In this case, the external headpiece may also include a retention flux guide positioned between the retention magnet and the circuit board. The retention flux guide may be configured to direct magnetic flux of the retention magnetic field away from the circuit board.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one example" or "an example" means that a particular feature, structure, or characteristic described in connection with the example is included in at least one example. The appearance of the phrase "in one example" in various places in the specification are not necessarily all referring to the same example.

Figure 1A:
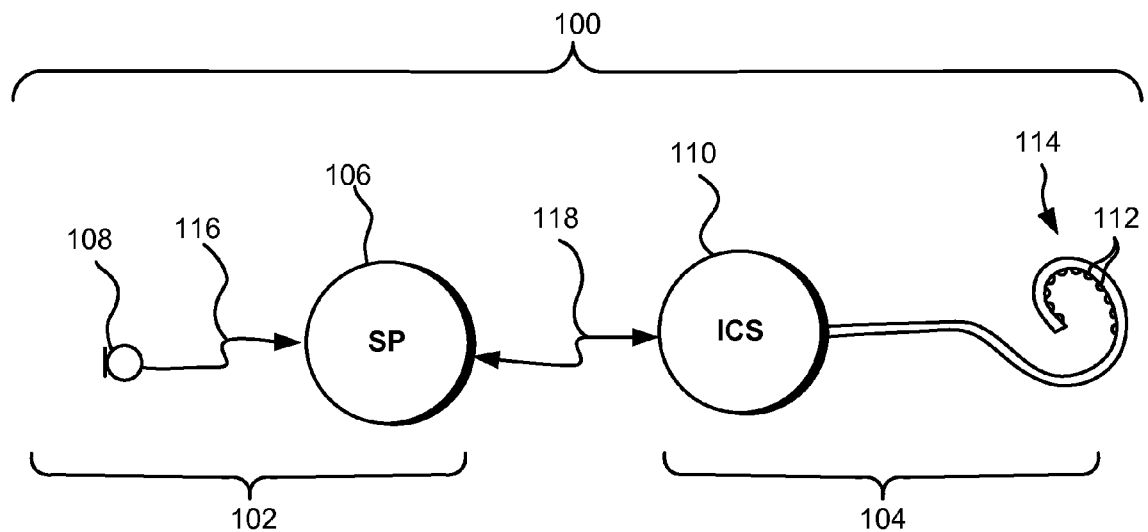
FIG. 1A illustrates an exemplary cochlear implant system according to principles described herein.

FIG. 1A illustrates an exemplary cochlear implant system 100. The cochlear implant system 100 of FIG. 1A includes a sound processor portion 102 and a cochlear stimulation portion 104. The sound processor portion 102 may include a sound processor 106, a microphone 108, and/or additional circuitry as best serves a particular application. The cochlear stimulation portion 104 may include an implantable cochlear stimulator 110, a number of electrodes 112 disposed on an electrode lead 114, and/or additional circuitry as best serves a particular application. The components within the sound processor portion 102 and the cochlear stimulation portion 104 will be described in more detail below.

The microphone 108 of FIG. 1A is configured to sense audio signals and convert the sensed signals to corresponding electrical signals. In some examples, the audio signal may include speech. The audio signal may additionally or alternatively include music, noise, and/or other sounds. The electrical signals are sent from the microphone 108 to the sound processor 106 via a communication link 116. Alternatively, the microphone 108 may be connected directly to, or integrated with, the sound processor 106. The sound processor 106 processes these converted audio signals in accordance with a selected sound processing strategy to generate appropriate stimulation parameters for controlling the implantable cochlear stimulator 110. These stimulation parameters may specify or define the polarity, magnitude, location (i.e., which electrode pair or electrode group receive the electrical stimulation), stimulation rate, timing (i.e., when the electrical stimulation is to be applied to a particular electrode pair), spectral tilt, and/or any other characteristic of the electrical stimulation that is generated by the implantable cochlear stimulator 110.

The electrode lead 114 shown in FIG. 1A is configured to be inserted within a duct of a cochlea. As shown in FIG. 1A, the electrode lead 114 includes a multiplicity of electrodes 112, e.g., sixteen electrodes, spaced along its length. It will be understood, however, that any number of electrodes 112 may be disposed on the electrode lead 114. The electrode lead 114 may be substantially as shown and described in U.S. Pat. Nos. 4,819,647 or 6,218,753, each of which is incorporated herein by reference in its respective entirety. As will be described in more detail below, electronic circuitry within the implantable cochlear stimulator 110 is configured to generate and apply electrical stimulation to one or more stimulation sites within the cochlea via selected stimulation channels (i.e., pairs or groups of the individual electrodes 112) in accordance with a specified stimulation strategy defined by the sound processor 106.

In some examples, the sound processor 106 and the microphone 108 comprise an external portion of the cochlear implant system 100, and the implantable cochlear stimulator 110 and the electrode lead 114 comprise an implantable portion of the system 100 that is implanted within a patient's body. In alternative embodiments, one or more portions of the sound processor 106 are included within the implantable portion of the cochlear implant system 100.

The implantable cochlear stimulator 110 and the sound processor 106 may be communicatively coupled via a suitable data or communication link 118, such as a telemetry communication link, as will be described in more detail below. It will be understood that the data communication link 118 may include a bi-directional communication link and/or one or more dedicated uni-directional communication links. In some examples, the external and implantable portions of the cochlear implant system 100 may each include one or more inductive coils configured to transmit and receive power and/or control signals via the communication link 118. The control signals may include, for example, the magnitude and polarity of electrical stimulation representing a sensed audio signal. The external coil may also transmit power from the external portion to the implantable portion of the cochlear implant system 100. Power transmitted to the implantable portion may be used to operate the implantable portion.

Figure 1B:
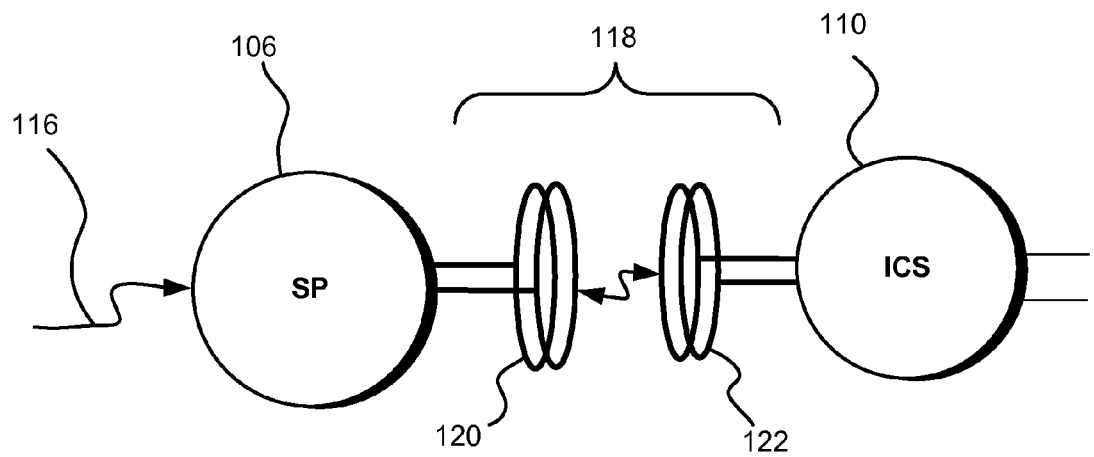
FIG. 1B illustrates a portion of an exemplary cochlear implant system according to principles described herein.

FIG. 1B illustrates a portion of an exemplary cochlear implant system showing a communication link 118 comprising a telemetry communication link that may be used in accordance with the present systems and methods. As illustrated in FIG. 1B, an external portion of the cochlear implant system 100 may include an external induction coil 120 and an implantable portion of the cochlear implant system 100 may include an implantable induction coil 122. The external induction coil 120 may be communicatively coupled to the sound processor 106 and the implantable induction coil 122 may be communicatively coupled to the implantable cochlear stimulator 110.

The external induction coil 120 and the implantable induction coil 122 may include any suitable type of coil capable of generating and/or receiving an electromagnetic field. For example, the external induction coil 120 and the implantable induction coil 122 may each include a metallic wire or tube wound in a coiled or otherwise looped configuration. An alternating current may be directed from the sound processor 106 through the external induction coil 120, thereby generating a magnetic field surrounding the external induction coil 120. The external induction coil 120 may be positioned near the implantable induction coil 122 such that the implantable induction coil 122 is positioned at least partially within the magnetic field generated by the external induction coil 120. The magnetic field generated by the external induction coil 120 may cause an electric current to be generated in the internal induction coil 120. The electric current generated in the internal induction coil 120 may be directed from the internal induction coil 120 to the implantable cochlear stimulator 110. Accordingly, an electric current generated by the sound processor 106 may be transferred to the implantable cochlear stimulator 110 through the communication link 118 comprising the external induction coil 120 and the implantable induction coil 122.

The communication link 118 may function as a telemetry link between the sound processor 106 and the implantable cochlear stimulator 110. For example, the external induction coil 120 may transmit one or more telemetry signals to the implantable induction coil 122 by generating a telemetry magnetic field as electric current is passed through the external induction coil 120. The telemetry magnetic field generated by the external induction coil 120 may produce an electric current in the implantable induction coil 122, as described above. The current generated in the implantable induction coil 122 by the telemetry magnetic field generated by the external induction coil 120 may be used to transfer signals representative of data and/or other information to the implantable cochlear stimulator 110 and/or may be used to transfer power to the implantable cochlear stimulator 110.

In some examples, the communication link 118 may be used to transmit telemetry signals from the implantable cochlear stimulator 110 to the sound processor 106. For example, data acquired by the electrodes 112 and/or status indicators generated by the cochlear stimulator 112 may be transmitted to sound processor 106 via the communication link 118. To this end, implantable induction coil 122 may transmit telemetry signals to the external induction coil 120 by generating a telemetry magnetic field. The implantable cochlear stimulator 110 may cause a current to flow through the implantable induction coil 122 to generate the telemetry magnetic field. The external induction coil 120 may be positioned at least partially within the telemetry magnetic field generated by the implantable induction coil 122. The magnetic field may cause an electric current to be generated in the external induction coil 120. The current generated in the external induction coil 120 may be used to transfer data and/or other signals to the sound processor 106.

The communication link 118 may include more than one external induction coil 120 and/or more than one implantable induction coil 122. For example, a first external induction coil and a first implantable induction coil may be used to transfer data and/or power from the sound processor 106 to the implantable cochlear stimulator 110. A second external induction coil and a second implantable induction coil may be used to transfer data from the implantable cochlear stimulator 110 to the sound processor 106.

Figure 2:
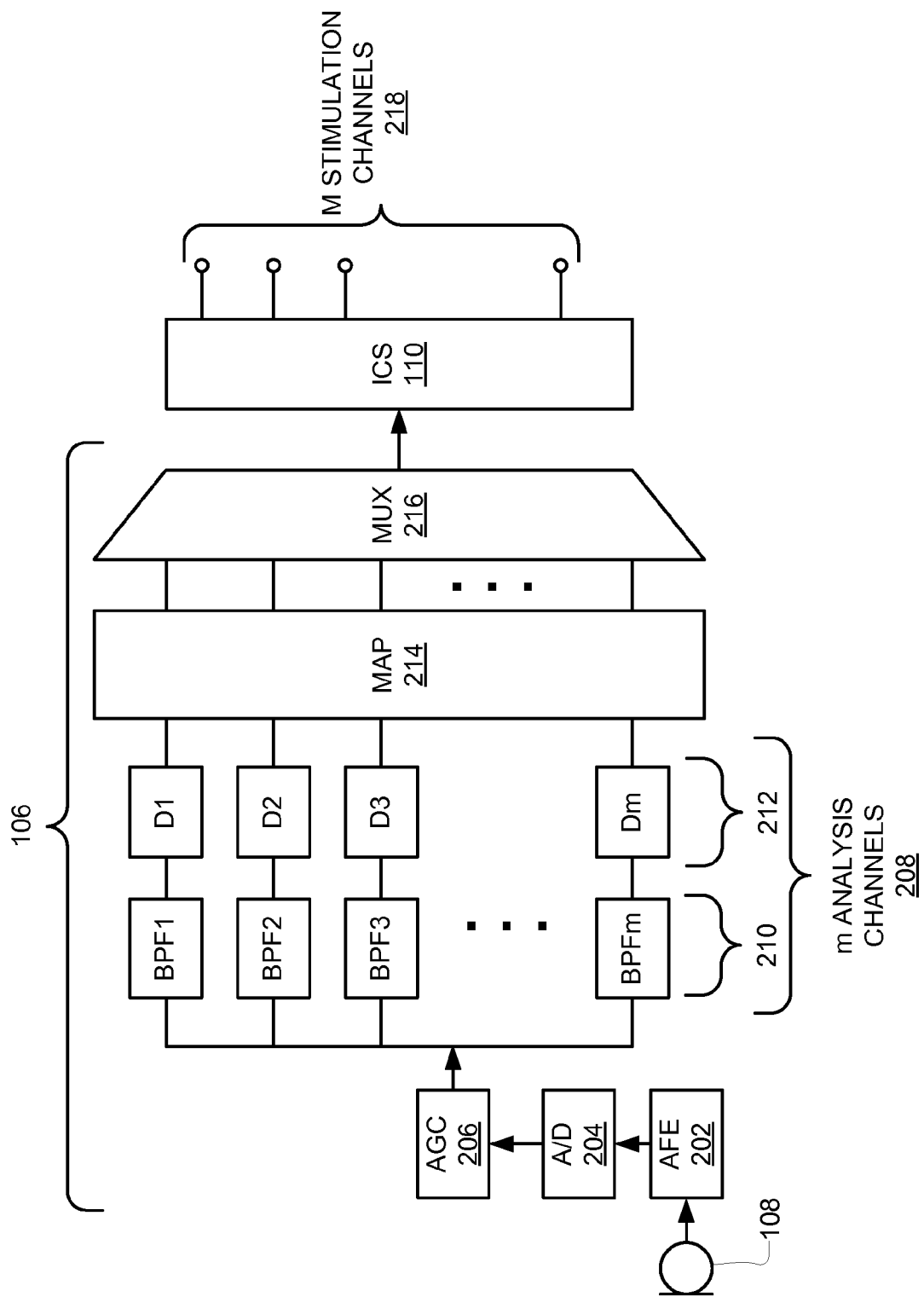
FIG. 2 is a functional block diagram of an exemplary sound processor and implantable cochlear stimulator according to principles described herein.

FIG. 2 is a functional block diagram of an exemplary sound processor 106 and implantable cochlear stimulator 110. The functions shown in FIG. 2 are merely representative of the many different functions that may be performed by the sound processor 106 and/or the implantable cochlear stimulator 110.

As shown in FIG. 2, the microphone 108 senses an audio signal, such as speech or music, and converts the audio signal into one or more electrical signals. These signals are then amplified in audio front-end (AFE) circuitry 202. The amplified audio signal is then converted to a digital signal by an analog-to-digital (A/D) converter 204. The resulting digital signal is then subjected to automatic gain control using a suitable automatic gain control (AGC) function 206.

After appropriate automatic gain control, the digital signal is then processed in one of a number of digital signal processing or analysis channels 208. For example, the sound processor 106 may include, but is not limited to, sixteen analysis channels 208. Each analysis channel 208 may respond to a different frequency band of the sensed audio signal due to a series of band pass filters 210.

As shown in FIG. 2, each of the m analysis channels 208 may also include an energy detection stage (D1-Dm) 212. Each energy detection stage 212 may include any combination of circuitry configured to detect the amount of energy contained within each of the m analysis channels 208. For example, each energy detection stage 212 may include a rectification circuit followed by an integrator circuit.

After energy detection, the signals within each of the m analysis channels 208 are forwarded to a mapping stage 214. The mapping stage 214 is configured to map the signals in each of the m analysis channels 208 to one or more of M stimulation channels 218. In other words, the information contained in the m analysis channels 208 is used to define the electrical stimulation pulses that are applied to the patient by the implantable cochlear stimulator 110 via the M stimulation channels 218. As mentioned previously, pairs or groups of individual electrodes 112 may make up the M stimulation channels 218.

In some examples, the mapped signals are serialized by a multiplexer 216 and transmitted to the implantable cochlear stimulator 110. The implantable cochlear stimulator 110 may then apply electrical stimulation via one or more of the M stimulation channels 218 to one or more stimulation sites within the duct of the patient's cochlea. As used herein, the term "stimulation site" will be used to refer to a target area or location to which the electrical stimulation is applied. For example, a stimulation site may refer to any location within a region of auditory nerve tissue (e.g., auditory nerve tissue 306 shown in FIG. 3).

Figure 3:
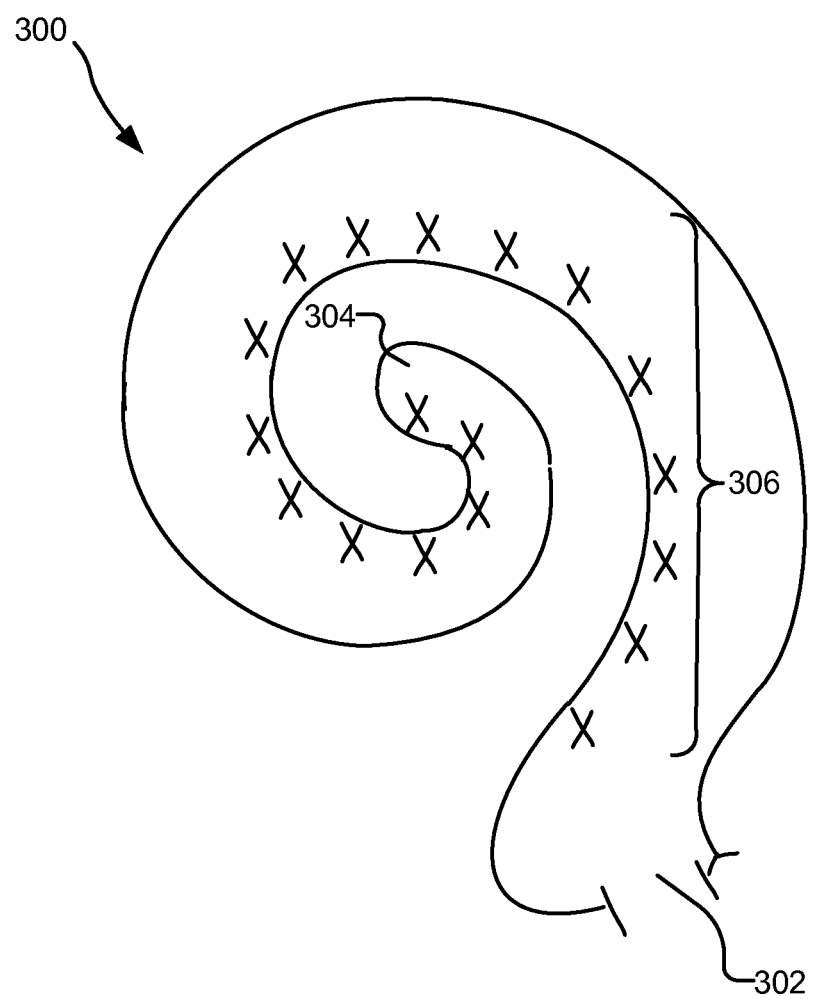
FIG. 3 illustrates a schematic structure of the human cochlea highlighting elements according to principles described herein.

FIG. 3 illustrates a schematic structure of the human cochlea 300. As shown in FIG. 3, the cochlea 300 is in the shape of a spiral beginning at a base 302 and ending at an apex 304. Within the cochlea 300 resides auditory nerve tissue 306, which is denoted by Xs in FIG. 3. The auditory nerve tissue 306 is organized within the cochlea 300 in a tonotopic manner. Low frequencies are encoded at the apex 304 of the cochlea 300 while high frequencies are encoded at the base 302. Hence, each location along the length of the cochlea 300 corresponds to a different perceived frequency. A cochlear prosthesis may therefore be implanted within a patient with sensorineural hearing loss and configured to apply electrical stimulation to different locations within the cochlea 300 to provide the sensation of hearing. For example, electrode lead 114 may be disposed within the cochlea 300 such that electrodes 112 contact auditory nerve tissue 306 within the cochlea 300. Electrical stimulation may be applied by the electrodes 112 to the auditory nerve tissue 306.

Figure 4:
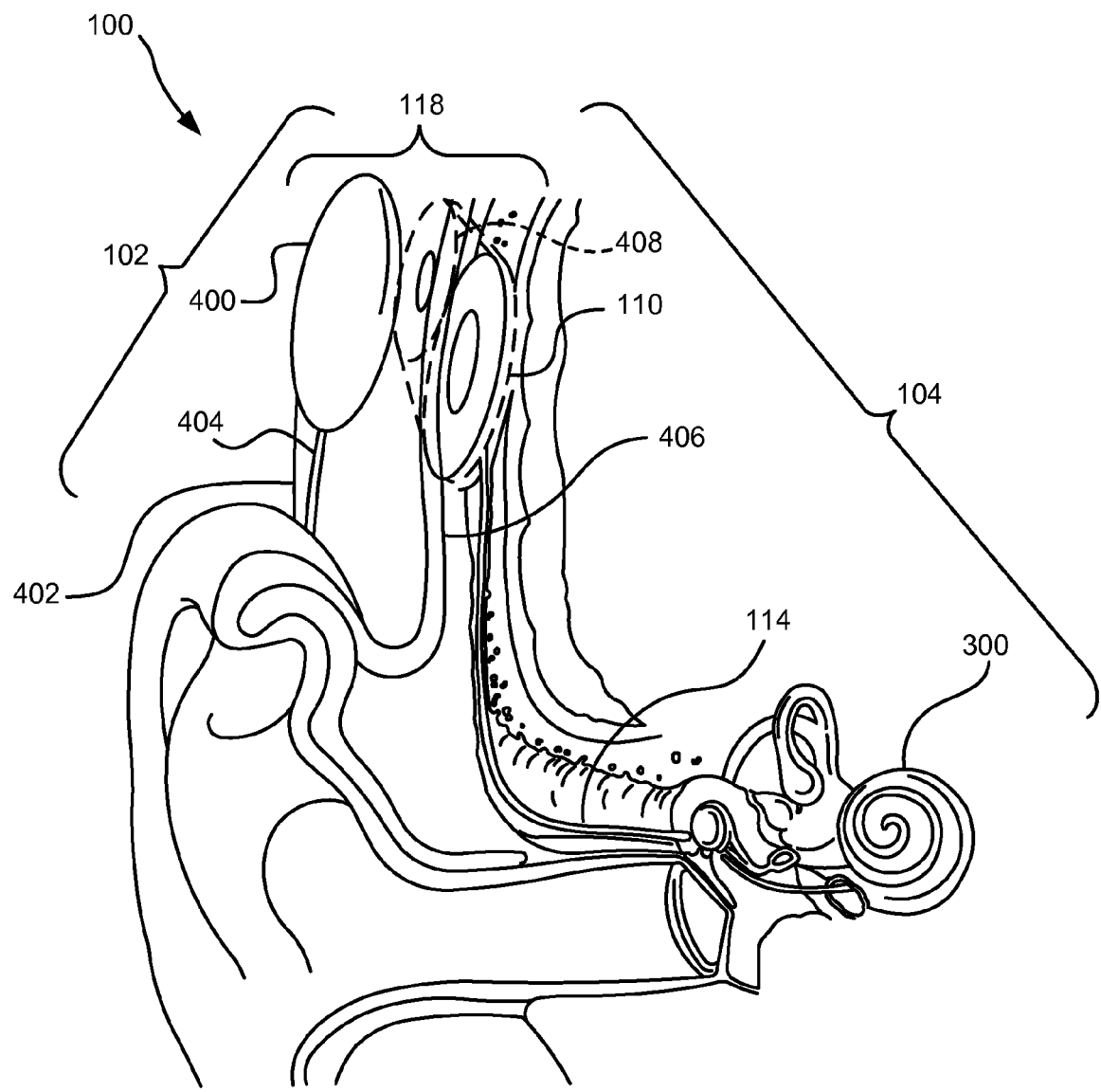
FIG. 4 illustrates an exemplary configuration of a cochlear implant system according to principles described herein.

FIG. 4 illustrates an exemplary configuration of cochlear implant system 100 that may be used to apply electrical stimulation one or more stimulation sites within the cochlea 300. As shown in FIG. 4, the external portion of the cochlear implant system 100 may include an external headpiece 400 configured to be worn on an exterior of a head 402 of the patient. The external headpiece 400 may include various components of the sound processor portion 102, including the external induction coil 122 (not shown), as will be described in greater detail below. The external headpiece 400 may additionally include electronic circuitry, such as circuitry comprising at least a portion of the sound processor 106. The external headpiece 400 may be electrically connected, either directly or indirectly, to a microphone 108 (not shown) positioned in or near the patient's ear via a communication line 404. The headpiece 400 may additionally include a retention magnet to position and maintain the headpiece 400 in a proper orientation on the head 402, as will be described in greater detail below.

As shown in FIG. 4, an implantable cochlear stimulator 110 may be disposed underneath the skin 406 of the patient. A lead 114 with a plurality of electrodes 112 disposed on a distal portion thereof may be coupled to the implantable cochlear stimulator 110 and positioned such that the electrodes 112 are disposed within the cochlea 300.

In some examples, the implantable cochlear stimulator 110 may include a receiver 408 configured to facilitate communication with the external headpiece 400. The receiver 408 may include the implantable induction coil 122 (not shown) described above.

The external induction coil 120 in the external headpiece 400 and the implantable induction coil 122 in the receiver 408 may form communication link 118. As described above, data and/or power may be transmitted between the sound processor portion 102 and the cochlear stimulation portion 104 via the communication link 118. For example, the external induction coil 120 in the external headpiece 400 may transmit a telemetry signal across the skin 406 to the implantable induction coil 122 in the receiver 408. Additionally or alternatively, the implantable induction coil 122 in the receiver 408 may transmit a telemetry signal across the skin 406 to the external induction coil 120 in the external headpiece 400.

Figure 5A:
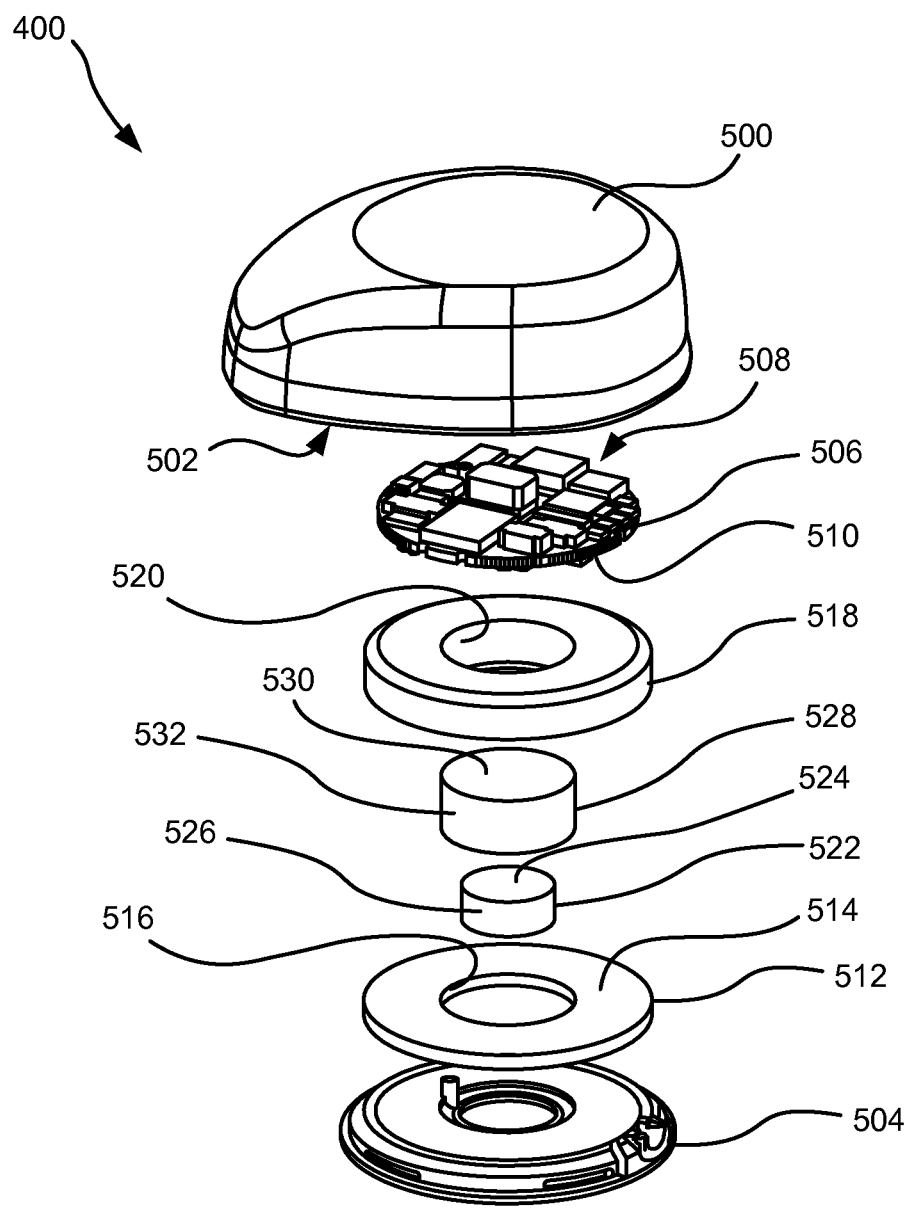
FIG. 5A is an exploded perspective view of an exemplary external headpiece according to principles described herein.
Figure 5B:
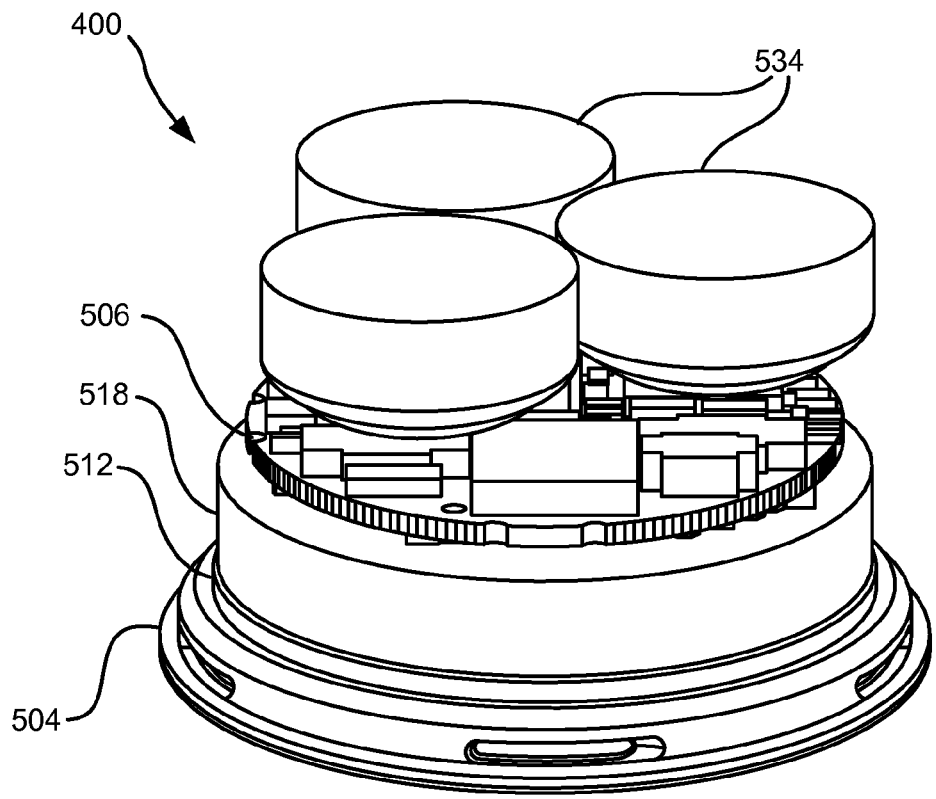
FIG. 5B is a perspective view of a portion of an exemplary external headpiece according to principles described herein.
Figure 5C:
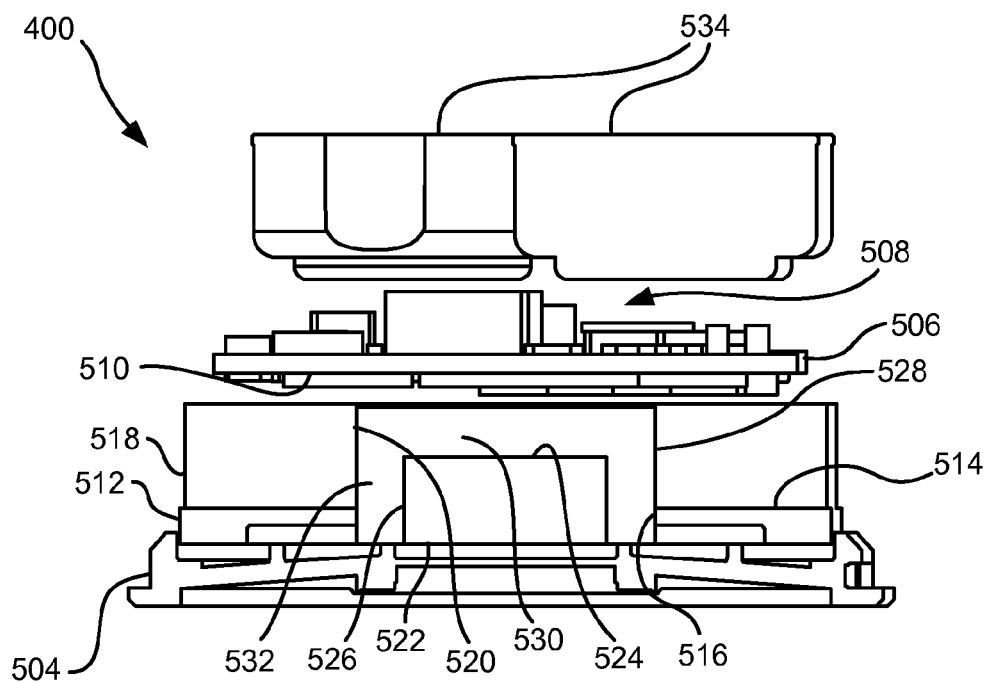
FIG. 5C is a cross-sectional side view of a portion of an exemplary external headpiece according to principles described herein.

FIGS. 5A-5C illustrate an exemplary external headpiece 400 that may be used in accordance with present systems and methods. The components shown in FIGS. 5A-5C are merely illustrative of the many different components that may be included within headpiece 400. Additional or alternative components may be included within headpiece 400 as may serve a particular application.

FIG. 5A is an exploded perspective view of the exemplary external headpiece 400 showing various components of the external headpiece 400. FIG. 5B is a perspective view of the exemplary external headpiece 400 shown without a headpiece cover. FIG. 5C is cross-sectional side view of the exemplary external headpiece 400 shown without a headpiece cover. As shown in FIGS. 5A-5C, the external headpiece 400 may include a headpiece cover 500 in which a headpiece cavity 502 is defined. The external headpiece 400 may additionally include a headpiece base 504 that may be attached to the headpiece cover 500. Components in the external headpiece 400 may be housed in the headpiece cavity 502 such that they are substantially surrounded by headpiece cover 500 and the headpiece base 504.

The external headpiece 400 may include a circuit board 506 (e.g., a printed circuit board) having electronic circuitry 508 disposed thereon. The electronic circuitry 508 may be disposed on any suitable portions of the circuit board 506. A bottom surface 510 of the circuit board 506 may face generally towards the headpiece base 504. The electronic circuitry 508 may include the sound processor 106 or at least a portion of the sound processor 106. The electronic circuitry 508 may be configured to direct the implantable cochlear stimulator 110 to generate and apply electrical stimulation to one or more stimulation sites within the cochlea 300 of a patient by transmitting control parameters (including, but not limited to, stimulation parameters) to the implantable cochlear stimulator 110 via communications link 118. The electronic circuitry 508 may additionally or alternatively be configured to transmit power to the implantable cochlear stimulator 110 and may be configured to receive data from the cochlear stimulator 110.

The external headpiece 400 may further include an induction coil 512 disposed below the bottom surface 510 of the circuit board 506. The induction coil 512 may include a metallic wire or tube wound in a coiled configuration. In some examples, the induction coil 512 may include a coiled wire arranged in a generally disc-shaped and/or annular-shaped holder. It will be recognized that the induction coil 512 may have any suitable size and shape as may serve a particular application.

The induction coil 512 may have a top surface 514 and an interior radial surface 516, as illustrated in FIG. 5A. The induction coil 512 may be seated in the headpiece base 504. Accordingly, the induction coil 512 may be in close proximity to the head 402 of the patient when the headpiece base 504 is adjacent to the head 402.

In some examples, the external headpiece 400 may additionally include a telemetry flux guide 518 positioned or disposed between the circuit board 506 and the induction coil 512. The telemetry flux guide 518 may have a generally annular shape with an inner radial surface 520 defining an aperture extending through a central portion of the telemetry flux guide 518. The telemetry flux guide may be adjacent to the bottom surface 510 of the circuit board 506 and the top surface 514 of the induction coil 512.

The telemetry flux guide 518 may include any material suitable for directing magnetic flux away from the circuit board 506. For example, the telemetry flux guide 518 may include a material having a relatively high resistivity that provides a low reluctance path for magnetic flux of the telemetry magnetic field. Additionally, the telemetry flux guide 518 may include a powdered material, such as a powdered metallic material having a relatively small particle size, in order to prevent the generation of eddy current in the telemetry flux guide 518. For example, eddy currents might be generated in a solid conductive material (as opposed to a powdered conductive material) in the presence of the telemetry magnetic field since the telemetry magnetic field is a changing magnetic field generated by an alternating current passing through the induction coil 512.

The powdered material in telemetry flux guide 518 may be held together using any suitable material, such as a polymer material. In some examples, the powdered metallic material may include iron and/or other ferrite materials. Additionally, the telemetry flux guide 518 may be suitable for frequencies of telemetry signals generated and/or received by the induction coil 512, such as, for example, an approximately 49 MHz telemetry signal and/or an approximately 10.7 MHz telemetry signal. A telemetry flux guide 518 including a material having a relative permeability (i.e., the ratio of the permeability of the alloy to the permeability of free-space) of approximately 9 may be suitable for a frequency range that includes 49 MHz and 10.7 MHz telemetry signals. However, it will be recognized that the telemetry flux guide 518 may have any other suitable relative permeability value as may serve a particular application. Additionally or alternatively, telemetry flux guide 518 may have a relatively high resistivity and a relatively small particle size in order to facilitate redirection of magnetic flux while minimizing the generation of eddy currents in the telemetry flux guide 518.

The telemetry flux guide 518 may be positioned and configured to direct magnetic flux of the magnetic field generated by the induction coil 512 away from the circuit board 506, as will be described in greater detail below. For example, a telemetry magnetic field may generated by the induction coil 512 to transmit a telemetry signal. Magnetic flux of the telemetry magnetic field may be directed away from the circuit board 506 by the telemetry flux guide 518, thereby protecting the electronic circuitry 508 on the circuit board 506 from the telemetry magnetic field. By directing the magnetic flux in the telemetry magnetic field away from the circuit board 506, energy losses from the induction coil 512 to the electronic circuitry 508 via the telemetry magnetic field may be minimized, thereby extending the life of batteries used to provide power to one or more components of the cochlear implant system 100.

In some examples, the external headpiece 400 may additionally or alternatively include a retention magnet 522 disposed between the circuit board 506 and the headpiece base 504. The retention magnet 522 may have a top surface 524 generally facing the bottom surface 510 of the circuit board 506. The retention magnet 522 may additionally have an outer radial surface 526. In some embodiments, the retention magnet 522 may be positioned in the external headpiece 400 such that the retention magnet 522 is at least partially surrounded by the induction coil 512 and/or the telemetry flux guide 518. Accordingly, the outer radial surface 526 of the retention magnet 522 may generally face the inner radial surface 516 of the induction coil 512 and/or the inner radial surface 520 of the telemetry flux guide 518. For example, the retention magnet 522 may be positioned in an aperture defined by the inner radial surface 520 extending through the telemetry flux guide 518.

The retention magnet 522 may be configured to produce a retention magnetic field for securing one or more components of a cochlear implant system 100 to a head 402 of a patient. For example, the retention magnet 522 may be disposed adjacent to the headpiece base 504 such that the retention magnet 522 is in close proximity to the head 402 of the patient when the headpiece base 504 is adjacent to the head 402. A portion of the cochlear stimulation portion 104 of the cochlear implant system 100, such as the receiver 408 shown in FIG. 4, may similarly include a magnet configured to magnetically couple with the retention magnet 522. Accordingly, when the headpiece base 504 is positioned adjacent to the head 402 of the patient near the receiver 408, the retention magnet 522 may be magnetically coupled to the magnet of the cochlear stimulation portion 104, thereby securing and/or orienting the external headpiece 400 on the head 402.

The external headpiece 400 may additionally or alternatively include a retention flux guide 528 positioned between the circuit board 506 and the retention magnet 522. The retention flux guide 528 may at least partially surround the retention magnet 522. As illustrated in FIGS. 5A and 5C, a top wall 530 of the retention flux guide 528 may be disposed in between and adjacent to the bottom surface 510 of the circuit board 506 and the top surface 524 of the retention magnet 522. Additionally, a side wall 532 of the retention flux guide 528 may at least partially surround the outer radial surface 526 of the retention magnet 522. The side wall 532 of the retention flux guide 528 may be adjacent to the outer radial surface 526 of the retention magnet 522, the inner radial surface 516 of the induction coil 512, and/or the inner radial surface 520 of the telemetry flux guide 518.

The retention flux guide 528 may include any material suitable for redirecting magnetic flux associated with a magnetic field produced by the retention magnet 522. For example, the retention flux guide 528 may include a material having a relatively high permeability. In some examples, the retention flux guide 528 may include a metallic material, such as a mu-metal alloy comprising nickel and iron. A relatively high permeability mu-metal alloy may have a relative permeability between approximately 60,000 and 300,000. For example, a mu-metal alloy may have a relative permeability of approximately 100,000. A high-permeability mu-metal alloy may include any suitable ratio of nickel and iron, such as, for example, a ratio of approximately 80% nickel and 20% iron. It will be recognized that the retention flux guide 528 may alternatively include any suitable material having any suitable relative permeability.

The retention flux guide 528 may be configured to direct magnetic flux of a retention magnetic field surrounding the retention magnet 522 away from the circuit board 506 and/or away from the telemetry flux guide 518. Accordingly, magnetic flux from the retention magnet 522 may be directed away from the circuit board 506, thereby protecting the electronic circuitry 508 on the circuit board 506 from the retention magnetic field.

As mentioned, the retention flux guide 528 may also direct magnetic flux of the retention magnetic field away from the telemetry flux guide 518, thereby preventing saturation of powdered metallic material in the telemetry flux guide 518 with magnetic flux from the retention magnet. Magnetic flux from the retention magnet 522 may significantly reduce the relative permeability of the powdered metallic material in the telemetry flux guide 518, reducing the effectiveness of the telemetry flux guide 518 in directing magnetic flux from the induction coil 512 away from the circuit board 506. Accordingly, the retention flux guide 528 may direct magnetic flux of the retention magnetic field away from the telemetry flux guide 518, thereby preventing magnetic flux from saturating the telemetry flux guide 518.

By directing magnetic flux away from the electronic circuitry 508 in the circuit board 506, the telemetry flux guide 518 and/or the retention flux guide 528 may enable the induction coil 512 and/or the retention magnet 522 to be located within the external headpiece 400 in relatively close proximity to the circuit board 506. Accordingly, the sound processor portion 102 of the cochlear implant system 100 may be made more compact by consolidating electronic and magnetic field emitting components within the headpiece as illustrated in FIGS. 5A-5C. This may increase the ease of use and comfort for a patient using the cochlear implant system 100 in comparison to conventional cochlear implant systems in which electronic circuitry is separated from the headpiece. For example, a consolidated assembly, such as that illustrated in FIGS. 5A-5C, may eliminate the need for a separate behind-the-ear assembly. Hence, the assembly illustrated in FIGS. 5A-5C may be referred to as a "one piece system headpiece".

In some embodiments, the cochlear stimulation portion 104 of a cochlear implant system 100 may additionally or alternatively include a retention flux guide and/or a telemetry flux guide for directing magnetic flux away from electronic components in the cochlear stimulation portion 104. For example, a receiver 408 in the cochlear stimulation portion 104 may include an induction coil and/or a retention magnet, similar to the external headpiece 400 as described above. A retention flux guide and/or a telemetry flux guide may be included in the receiver 408 to redirect magnetic flux away from electronic circuitry that may be located in close proximity to the induction coil and/or the retention magnet.

Additionally, as illustrated in FIGS. 5B and 5C, the external headpiece 400 may include one or more batteries 534 to power the sound processor portion 102 and/or the cochlear stimulation portion 102 of the cochlear implant system 100. Batteries 534 may be disposed within the headpiece cover cavity 502 of the headpiece cover 500 and may be located adjacent circuit board 506. In some embodiments, batteries 534 may be located outside of the external headpiece 400.

Figure 6:
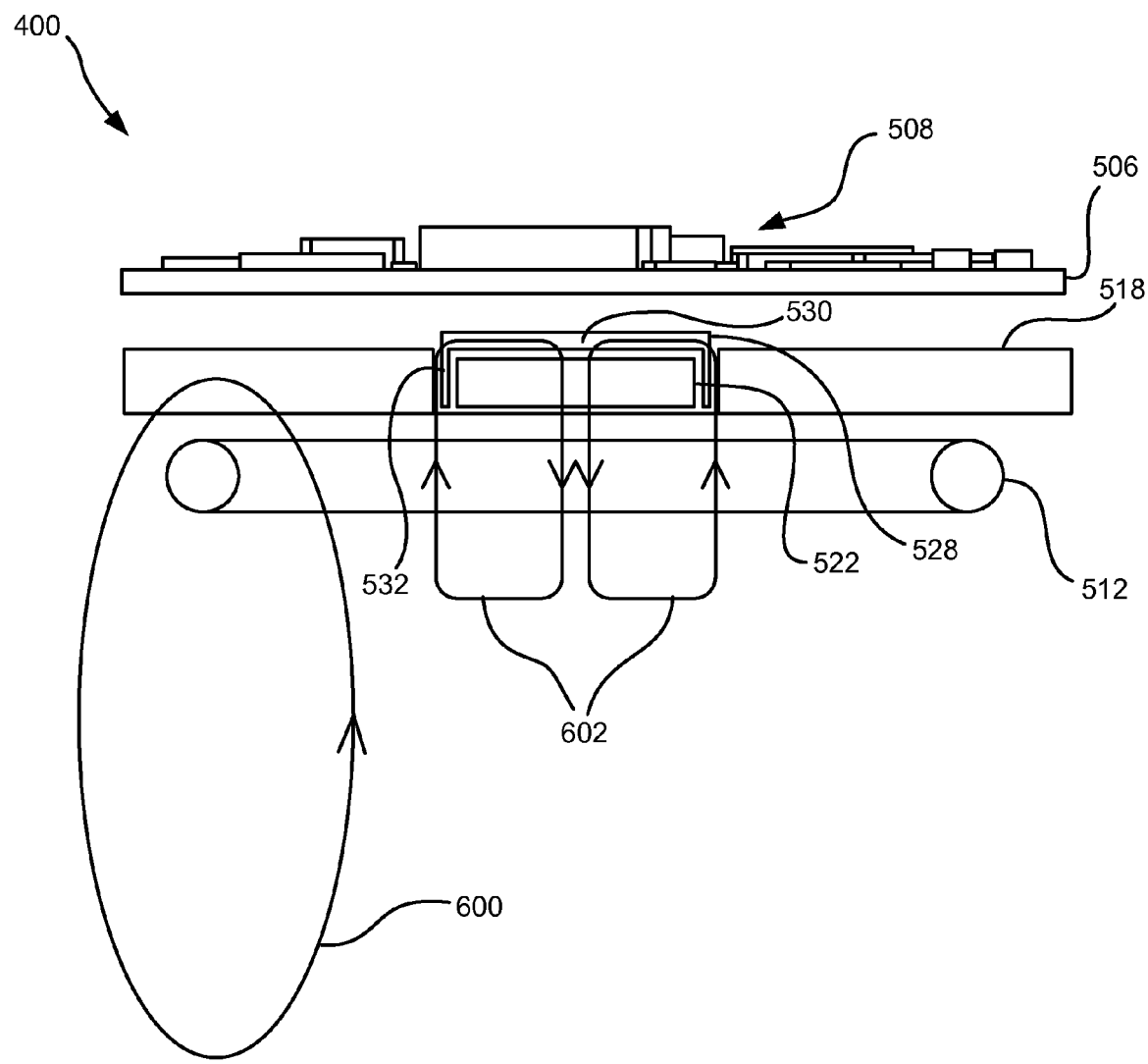
FIG. 6 illustrates magnetic flux surrounding an induction coil and a retention magnet in an exemplary external headpiece according to principles described herein.

FIG. 6 illustrates magnetic flux surrounding an induction coil 512 and a retention magnet 522 in an exemplary external headpiece 400 in accordance with the present systems and methods. As illustrated in FIG. 6, magnetic flux 600 may surround the induction coil 512. The magnetic flux 600 is represented as a flux path surrounding the induction coil 512. Additionally, magnetic flux 602 may pass through and surround retention magnet 522. The magnetic flux 602 is represented as flux paths surrounding and passing through the retention magnet 522. It will be recognized that additional flux paths other than those illustrated in FIG. 6 may be associated with the telemetry magnetic field surrounding the induction coil 512 and the retention magnetic field surrounding the retention magnet 522.

The telemetry flux guide 518 may provide a low reluctance path for the magnetic flux 600 surrounding the induction coil 512. As illustrated in FIG. 6, the path of the magnetic flux 600 may be directed through the telemetry flux guide 518 such that a path of the magnetic flux 600 between the induction coil 512 and the circuit board 506 may be shortened. The magnetic flux 600 of the telemetry magnetic flux field surrounding the induction coil 512 may therefore be redirected by the telemetry flux guide 518 such that the magnetic flux 600 is substantially prevented from reaching the circuit board 506, thereby reducing or eliminating magnetic flux passing through the electronic circuitry 508.

The retention flux guide 528 may provide a high permeability path for the magnetic flux 602 surrounding and passing through the retention magnet 522. As illustrated in FIG. 6, the path of the magnetic flux 602 may be directed through the retention flux guide 528 such that a path of the magnetic flux 602 passes generally through and/or along the top wall 530 and/or the side wall 532 of the retention flux guide 528. Accordingly, a path of the magnetic flux 602 between the induction coil 512 and the circuit board 506 may be shortened. Similarly, a path of the magnetic flux 602 between the retention magnet 522 and the telemetry flux guide 518 may be shortened. The magnetic flux 602 of the retention magnetic flux field surrounding and passing through the retention magnet 522 may therefore be redirected by the retention flux guide 528 such that the magnetic flux 602 is substantially prevented from reaching the circuit board 506 and/or the telemetry flux guide 518, thereby reducing or eliminating magnetic flux from the retention magnet passing through the electronic circuitry 508 and/or the telemetry flux guide 518.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A cochlear implant system comprising:
an external headpiece configured to be secured to an exterior of a head of a patient and that houses
1) a circuit board comprising electronic circuitry configured to generate one or more signals comprising one or more stimulation parameters configured to direct an implantable cochlear stimulator implanted within said patient to apply electrical stimulation to one or more stimulation sites within said patient;
2) an induction coil configured to transmit said one or more signals to said implantable cochlear stimulator by generating a telemetry magnetic field; and
3) a telemetry flux guide positioned between and in direct contact with a top surface of said induction coil and a bottom surface of said circuit board;
wherein said telemetry flux guide is configured to direct magnetic flux of said telemetry magnetic field away from said circuit board.

2. The cochlear implant system of claim 1, wherein the external headpiece further comprises a retention magnet configured to produce a retention magnetic field for securing one or more components of said cochlear implant system to a head of said patient.

3. The cochlear implant system of claim 2, wherein said retention magnet is positioned in an aperture extending through said telemetry flux guide.

4. The cochlear implant system of claim 2, wherein the external headpiece further comprises a retention flux guide positioned between said retention magnet and said circuit board, wherein said retention flux guide is configured to direct magnetic flux of said retention magnetic field away from said circuit board.

5. The cochlear implant system of claim 4, wherein at least a portion of said retention flux guide is positioned between said retention magnet and said telemetry flux guide.

6. The cochlear implant system of claim 4, wherein said retention flux guide comprises a metal having a comparatively high relative permeability.

7. The cochlear implant system of claim 1, wherein said telemetry flux guide has an annular shape.

8. The cochlear implant system of claim 1, wherein said telemetry flux guide comprises a material having a relatively high resistivity.

9. The cochlear implant system of claim 1, wherein said telemetry flux guide comprises a powdered metallic material.

10. The cochlear implant system of claim 9, wherein said powdered metallic material comprises a ferrite material.

11. The cochlear implant system of claim 9, wherein said powdered metallic material comprises iron.

12. A cochlear implant system comprising:
an external headpiece configured to be secured to an exterior of a head of a patient and that houses
1) a circuit board comprising electronic circuitry configured to generate one or more signals comprising one or more stimulation parameters configured to direct an implantable cochlear stimulator implanted within said patient to apply electrical stimulation to one or more stimulation sites within said patient;
2) an induction coil configured to transmit said one or more signals to said implantable cochlear stimulator by generating a telemetry magnetic field;
3) a telemetry flux guide positioned between and in direct contact with a top surface of said induction coil and a bottom surface of said circuit board;
4) a retention magnet configured to produce a retention magnetic field for securing one or more components of said cochlear implant system to a head of said patient; and
5) a retention flux guide positioned between said retention magnet and said circuit board;
wherein said retention flux guide is configured to direct magnetic flux of said retention magnetic field away from said circuit board, and wherein said retention magnet and said retention flux guide are positioned within an aperture extending through said telemetry flux guide.

13. The cochlear implant system of claim 12, wherein said retention flux guide comprises a metal having a comparatively high relative permeability.

14. The cochlear implant system of claim 12, wherein said retention flux guide comprises a nickel-iron alloy.

15. The cochlear implant system of claim 12, wherein said retention flux guide has a relative permeability between approximately 60,000 and approximately 300,000.

16. A cochlear implant system comprising:
- an external headpiece configured to be secured to an exterior of a head of a patient and comprising:
  1) a circuit board comprising electronic circuitry;
  2) a first induction coil configured to transmit a telemetry signal by generating a telemetry magnetic field; and
  3) a telemetry flux guide positioned between and in direct contact with a top surface of said induction coil and a bottom surface of said circuit board;
  wherein said telemetry flux guide is configured to direct magnetic flux of said telemetry magnetic field away from said circuit board; and
- an implantable cochlear portion implanted within said patient and comprising:
  1) an implantable cochlear stimulator that includes a receiver comprising a second induction coil configured to receive said telemetry signal; and
  2) a lead electrically coupled to said receiver, said electrode lead comprising a plurality of electrodes configured to be in communication with one or more stimulation sites within a cochlea of said patient;
  wherein said electronic circuitry is configured to generate one or more signals configured to direct said implantable cochlear stimulator to generate and apply electrical stimulation to said one or more stimulation sites via said plurality of electrodes.

17. The cochlear implant system of claim 16, wherein said external headpiece further comprises:
- a retention magnet configured to produce a retention magnetic field for securing one or more components of said cochlear implant system to said head of said patient; and
- a retention flux guide positioned between said retention magnet and said circuit board;
- wherein said retention flux guide is configured to direct magnetic flux of said retention magnetic field away from said circuit board.

18. The cochlear implant system of claim 17, wherein:
- said external headpiece is configured to be disposed externally on said head of said patient and said implantable cochlear stimulator is configured to be disposed internally within said head of said patient; and
- said retention magnet is configured to be magnetically coupled to a portion of said implantable cochlear stimulator.

19. The cochlear implant device of claim 16, wherein:
- said external headpiece is configured to be disposed externally on said head of said patient; and
- said implantable cochlear stimulator is configured to be disposed internally within said head of said patient such that said second induction coil is positioned at least partially within said telemetry magnetic field generated by said first induction coil.

20. An external headpiece configured to be secured to an exterior of a head of a patient for use in a cochlear implant system, said external headpiece comprising:
1) a circuit board comprising electronic circuitry configured to generate one or more signals comprising one or more stimulation parameters configured to direct an implantable cochlear stimulator implanted within said patient to apply electrical stimulation to one or more stimulation sites within said patient;
2) an induction coil configured to transmit said one or more signals to said implantable cochlear stimulator by generating a telemetry magnetic field; and
3) a telemetry flux guide positioned between and in direct contact with a top surface of said induction coil and a bottom surface of said circuit board;
wherein said telemetry flux guide is configured to direct magnetic flux of said telemetry magnetic field away from said circuit board.

21. The external headpiece of claim 20, further comprising:
- a retention magnet configured to produce a retention magnetic field for securing one or more components of said cochlear implant system to said head of said patient; and
- a retention flux guide positioned between said retention magnet and said circuit board;
- wherein said retention flux guide is configured to direct magnetic flux of said retention magnetic field away from said circuit board.

* * * * *